United States Patent
Reynolds et al.

(10) Patent No.: US 9,956,143 B2
(45) Date of Patent: May 1, 2018

(54) SYRINGE APPARATUS FOR TRANSFERRING LIQUIDS INTO AND OUT OF A VIAL HAVING A SEPTUM

(71) Applicant: PharmaC, LLC, Jackson, WY (US)

(72) Inventors: Timothy C. Reynolds, Sunnyvale, CA (US); David R. Pestotnik, Casper, WY (US); Christopher M. Tice, Jackson, WY (US)

(73) Assignee: PharmaC, LLC, Jackson, WY (US)

( * ) Notice: Subject to any disclaimer, the term of this patent is extended or adjusted under 35 U.S.C. 154(b) by 42 days.

(21) Appl. No.: 15/182,333

(22) Filed: Jun. 14, 2016

(65) Prior Publication Data
US 2017/0354572 A1   Dec. 14, 2017

(51) Int. Cl.
*A61J 1/20* (2006.01)
*A61J 1/14* (2006.01)
*B65B 3/00* (2006.01)

(52) U.S. Cl.
CPC ........... *A61J 1/2096* (2013.01); *A61J 1/1406* (2013.01); *A61J 1/201* (2015.05); *A61J 1/2082* (2015.05); *B65B 3/003* (2013.01)

(58) Field of Classification Search
CPC ........ A61J 1/2096; A61J 1/201; A61J 1/2082; A61J 1/1406; B65B 3/003
See application file for complete search history.

(56) References Cited

U.S. PATENT DOCUMENTS

| | | | | |
|---|---|---|---|---|
| 2,316,095 A * | 4/1943 | Mead, Jr. | ................ | A61M 5/24 604/209 |
| 4,318,400 A * | 3/1982 | Peery | .................... | A61M 5/141 128/DIG. 12 |
| 4,822,339 A * | 4/1989 | Tran | .................... | A61M 5/1407 604/246 |
| 5,002,528 A * | 3/1991 | Palestrant | ........... | A61M 3/0241 604/246 |
| 5,181,909 A * | 1/1993 | McFarlane | ............ | A61M 5/315 604/191 |
| 5,211,632 A * | 5/1993 | Tsukada | ................ | A61M 5/152 222/212 |
| 6,238,372 B1 * | 5/2001 | Zinger | .................. | A61J 1/2089 604/246 |
| 6,379,340 B1 * | 4/2002 | Zinger | .................. | A61J 1/2089 604/246 |
| 6,749,590 B2 * | 6/2004 | Niedospial, Jr. | ..... | A61M 5/3129 604/110 |
| 7,882,863 B2 * | 2/2011 | Pestotnik | .............. | A61J 1/2089 141/27 |
| 8,268,263 B2 * | 9/2012 | Campbell | ............... | B01L 3/563 141/329 |
| 8,869,635 B2 * | 10/2014 | Daniel | .................. | A61J 1/2096 73/864.74 |
| 9,321,545 B2 * | 4/2016 | Pestotnik | .............. | A61J 1/2096 |
| 9,617,020 B2 * | 4/2017 | Lanigan | ................. | B65B 3/003 |

(Continued)

*Primary Examiner* — Nicolas A Arnett
(74) *Attorney, Agent, or Firm* — Samuel M. Freund; Cochran Freund & Young LLC

(57) ABSTRACT

An apparatus for transferring a chosen quantity of medication from a vial to a container under sterile conditions is described. The present invention further facilitates dissolving solid medications contained in the vial or diluting concentrated medications contained in the vial, and transferring the resulting solutions to the container. The container may be an intravenous infuser.

28 Claims, 7 Drawing Sheets

(56) References Cited

U.S. PATENT DOCUMENTS

| | | | |
|---|---|---|---|
| 2002/0087118 A1* | 7/2002 | Reynolds | A61J 1/2089 604/82 |
| 2002/0104584 A1* | 8/2002 | Spero | A61J 1/2089 141/329 |
| 2003/0036725 A1* | 2/2003 | Lavi | A61M 5/2066 604/91 |
| 2004/0254525 A1* | 12/2004 | Uber, III | A61M 5/007 604/67 |
| 2009/0082751 A1* | 3/2009 | Reynolds | A61J 1/2089 604/413 |
| 2010/0310426 A1* | 12/2010 | Campbell | B01L 3/563 422/516 |
| 2011/0106021 A1* | 5/2011 | Ruegg | A61K 8/64 604/290 |
| 2011/0106045 A1* | 5/2011 | Reynolds | A61J 1/2096 604/413 |
| 2011/0212517 A1* | 9/2011 | Dahm | B01J 19/249 435/306.1 |
| 2012/0103468 A1* | 5/2012 | Terwilliger | A61J 1/1437 141/346 |
| 2012/0238969 A1* | 9/2012 | Ruegg | A61K 8/64 604/290 |
| 2012/0302986 A1* | 11/2012 | Brem | A61J 1/2096 604/414 |
| 2012/0330280 A1* | 12/2012 | Reynolds | A61J 1/2096 604/520 |
| 2015/0013836 A1* | 1/2015 | Pestotnik | A61J 1/2096 141/27 |
| 2015/0101708 A1* | 4/2015 | Reynolds | A61J 1/2096 141/27 |

\* cited by examiner

SYRINGE APPARATUS FOR TRANSFERRING LIQUIDS INTO AND OUT OF A VIAL HAVING A SEPTUM

BACKGROUND OF THE INVENTION

Medications are often stored in powdered form under inert gases, or as a concentrated liquid which may require refrigeration. Before use, the medication must be dissolved, diluted or warmed. The processed medication often has only short-term stability, and must be used rapidly. Premixed medications may be sent to a user by priority mail or other rapid shipping service; however, this adds significant cost to the user, and the delay incurred may reduce the effectiveness of the medication. Complicated mixing apparatus and protocols currently in use for mixing and diluting medications in a sterile environment have generated difficulty for patients who self-administer medications while housebound. Other situations which require medications to be mixed or diluted include trauma units, hospitals and doctor's offices where nurses and other medical staff must quickly and accurately mix medications while maintaining sterile conditions.

SUMMARY OF THE INVENTION

In accordance with embodiments of the present invention, as embodied and broadly described herein, the apparatus for transferring liquids into and out of a vial having a septum, hereof includes: a barrel having a bore with an elliptical cross section having a major axis and a minor axis, an open end, and a closed end, the closed end forming a port through which fluids flow; a plunger including: an elongated shaft having an axis; a first end, a first disk-shaped member forming a flat second end thereof, and an external surface between the first end and the first disk-shaped member; and having a first bore along the axis opening through both the first end and through the second end of the elongated shaft; the flat second end having a cylindrical stub thereon having a second axis collinear with the axis of the elongated shaft, and a second bore along the second axis in fluid communication with the first bore, the cylindrical stub having an outer surface and a longitudinal channel therein between the second bore and the outer surface thereof; a flexible stopper having an elliptical cross section adapted to slidably move within the bore of the barrel without rotating therein, and to provide a fluid seal therewith; a first end and a second end, a cylindrical-shaped interior portion opening to the first end and adapted to rotatably receive the first disk-shaped member; a recess adjacent to the cylindrical-shaped interior portion having an interior surface adapted to rotatably receive the cylindrical stub and to provide a fluid seal therewith; and a third bore passing between the interior surface of the recess through the second end of said stopper, such that when the elongated shaft is rotated to a chosen position, the third bore is in fluid contact with the longitudinal channel of the stub, and through the channel to the second bore; and a dispensing member having a septum-piercing spike at one end thereof with a fourth bore and a fifth bore exiting the spike, the fourth bore passing through the dispensing member and exiting a second end thereof, the dispensing member being attached to or integrally formed with the first end of the elongated shaft such that the fourth bore is in fluid communication with the first bore, the fifth bore entering said dispensing member and exiting through an exterior face thereof, forming thereby a pressure relief port.

In another aspect of embodiments of the present invention, the apparatus for transferring liquids into and out of a vial having a septum hereof includes: a barrel having a circular bore with an axis, having a chosen circumference and at least one flat portion along the circumference of the bore extending over the length thereof, an open end, and a closed end, the closed end forming a port through which fluids flow; a plunger including: an elongated shaft having an axis; a first end, a first disk-shaped member forming a flat second end thereof, and an external surface between the first end and the first disk-shaped member; and having a first bore along the axis opening through both the first end and through the second end of the elongated shaft; the flat second end having a cylindrical stub thereon having a second axis collinear with the axis of the elongated shaft, and a second bore along the second axis in fluid communication with the first bore, the cylindrical stub having an outer surface and a longitudinal channel therein between the second bore and the outer surface thereof; a flexible stopper having at least one flat portion on the circumference thereof over a portion of the length of said stopper adapted to engage the at least one flat portion along the circumference of the bore such that the stopper slidably moves within the bore of the barrel without rotating therein, and to provide a fluid seal therewith; a first end and a second end, a cylindrical-shaped interior portion opening to the first end and adapted to rotatably receive the first disk-shaped member; a recess adjacent to the cylindrical-shaped interior portion having an interior surface adapted to rotatably receive the cylindrical stub and to provide a fluid seal therewith; and a third bore passing between the interior surface of the recess through the second end of the stopper, such that when said shaft is rotated to a chosen position, the third bore is in fluid contact with the longitudinal channel of the stub, and through the channel to the second bore; and a dispensing member having a septum-piercing spike at one end thereof with a fourth bore and a fifth bore exiting the spike, the fourth bore passing through the dispensing member and exiting a second end thereof, the dispensing member being attached to or integrally formed with the first end of the elongated shaft such that the fourth bore is in fluid communication with the first bore, the fifth bore entering the dispensing member and exiting through an exterior face thereof, forming thereby a pressure relief port.

In yet another aspect of embodiments of the present invention, the apparatus for transferring liquids into and out of a vial having a septum hereof includes: a barrel having a bore with an elliptical cross section having a major axis and a minor axis, an open end, and a closed end, the closed end forming a port through which fluids flow, the bore further having two opposing inward facing lips having an inner surface having a radius in the vicinity of the open end thereof along at least a portion of the bore in the vicinity of the minor axis; a plunger including: an elongated shaft having an axis; a first end, a first disk-shaped member forming a flat second end thereof, and an external surface between the first end and the first disk-shaped member; and having a first bore along the axis opening through both the first end and through the second end of the elongated shaft; the flat second end having a cylindrical stub thereon having a second axis collinear with the axis of the elongated shaft, and a second bore along the second axis in fluid communication with the first bore, the cylindrical stub having an outer surface and a longitudinal channel therein between the second bore and the outer surface thereof; a first pair of elongated flat plunger stabilizing members each stabilizer member having an inner edge radially attached to opposite sides of the surface of the elongated shaft along at least a portion of the long dimension thereof defining a first plane, and an outer edge opposite to the inner edge; a second pair of elongated flat stabilizer members each member having an inner edge radially attached to opposite sides of the surface of the elongated shaft along at least a portion of the long dimension thereof defining a second plane perpendicular to the first plane, and an outer edge opposite to the inner edge, wherein the outer edges of the first pair of stabilizer members and the second pair of stabilizer members are disposed within a circle having a radius smaller than the minor axis of the bore and larger than the radius of the inner surface of the lips of the barrel; a flexible stopper having an elliptical cross section adapted to slidably move within the bore of the barrel without rotating therein, and to provide a fluid seal therewith; a first end and a second end, a cylindrical-shaped interior portion opening to the first end and adapted to rotatably receive the first disk-shaped member; a recess adjacent to the cylindrical-shaped interior portion having an interior surface adapted to rotatably receive the cylindrical stub and to provide a fluid seal therewith; and a third bore passing between the interior surface of the recess through the second end of the stopper; wherein the rotation of the first disk-shaped member is confined to a chosen amount in the cylindrical-shaped interior portion when the elongated shaft is rotated about the long dimension thereof in one direction with one pair of stabilizer members contacting the lips, and in the opposite direction with the other pair of stabilizer members contacting the lips, such that the third bore is in fluid contact with the longitudinal channel of the stub, and through the channel to the second bore in a portion of the chosen amount of rotation; and a dispensing member having a septum-piercing spike at one end thereof with a fourth bore and a fifth bore exiting the spike, the fourth bore passing through the dispensing member and exiting a second end thereof, the dispensing member being attached to or integrally formed with the first end of the elongated shaft such that the fourth bore is in fluid communication with the first bore, the fifth bore entering the dispensing member and exiting through an exterior face thereof, forming thereby a pressure relief port.

Benefits and advantages of the present invention include, but are not limited to, providing a device for accurately and rapidly mixing medical solutions and dissolving powdered medications forming solutions, and introducing these solutions into containers while maintaining the sterility of both the starting materials and the final product.

BRIEF DESCRIPTION OF THE DRAWINGS

The accompanying drawings, which are incorporated in and form a part of the specification, illustrate two embodiments of the present invention and, together with the description, serve to explain the principles of the invention.

FIG. 3A is schematic representation of the side view of the stopper shown in FIG. 1B hereof, while

FIG. 4A is a schematic representation of a side view of the barrel of the present invention illustrating a valve attached to the exit port Luer connection thereof for stopping fluid flow or permitting fluid to flow therethrough, while

FIG. 5A is a schematic representation of the top view of another embodiment of the barrel of the present invention, while

DETAILED DESCRIPTION

Briefly, the present invention includes a closed apparatus for mixing, diluting and transferring sterile medications from a vial having a septum to an infuser container having a luer lock filling port. The mixing/diluting system permits the dissolution of medications that are shipped and stored as solids, and the dilution of medications that are shipped and stored as concentrated liquids. Chosen doses of medications can also be introduced into the infuser container for self-dosing patient use as well as for other uses. The apparatus may be accurately and rapidly used, maintains the sterility of the medications, and may easily be assembled from readily available parts.

Figure 1A:
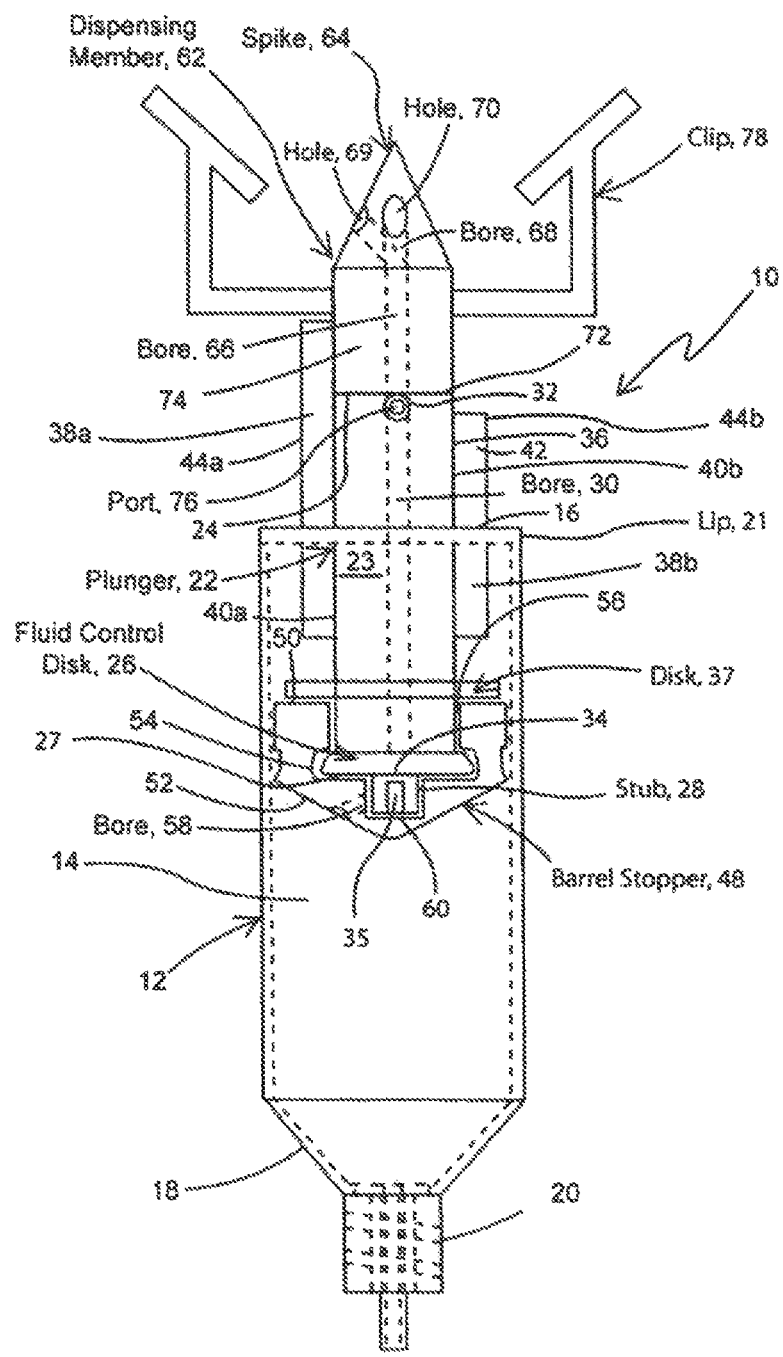
FIG. 1A is a schematic representation of a front view of one embodiment of the present apparatus for mixing liquid medications and dissolving powdered medications, and for introducing the resulting solutions into a container, illustrating the wider side of the elliptical barrel member.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1A, a schematic representation of a front view of an embodiment of apparatus, 10, of the present invention for mixing liquid medications and dissolving powdered medications, and for introducing the resulting solutions into an infuser container or otherwise dispensing the solutions is shown. Barrel, 12, has bore, 14, having an elliptical cross section having a major axis and a minor axis, the wider side of barrel 12 being shown in FIG. 1A an open end, 16, and a closed end, 18. The closed end forms fluid exit port, 20, adapted for attaching a container, and shown in FIG. 1A as a Luer connection, as an example. The container may be an infuser, or an IV Piggyback infuser, as examples (not shown in FIG. 1A). At least one inward facing lip, 21, having inner surface, 19, is formed along at least a portion of the inner wall of barrel 12 in the region corresponding to the minor axis, for preventing plunger, 22, from accidentally being pulled out of bore 14, as will be explained hereinbelow. Inner surface 19 of lip 21 effectively reduces the minor axis of bore 14 at open end 16 of barrel 12 to a dimension smaller than that of the minor axis, and is hereinafter referred to as the radius of the inner surface of lip 21. Plunger 22 includes elongated shaft, 23, having first end, 24, first circular disk-shaped member, 26, having a first diameter and forming a second flat end thereof, 27, the second flat end having cylindrical stub, 28, axially formed thereon. Bore, 30, within shaft 23, opens through first end 24 at hole, 32, and through the second end at hole, 34, which opens into slot, 35, in stub 28. External surface, 36, of shaft 23 is located between the first end 24 and disk-shaped member 26 thereof. Second circular disk-shaped member, 37, having a diameter slightly smaller than the minor axis of bore 14 and larger than that first disk-shaped member 26 is formed on external surface, 36, near to first disk-shaped member 26. Barrel 12 may include graduation marks on the surface thereof to permit filling thereof with a chosen quantity of fluid.

Shaft 23 has a first pair of elongated flat piston stabilizer members, 38a, and, 38b, each member having inner edge, 40a, and, 40b, respectively, radially attached to opposite sides of surface 36 of plunger 22 along at least a portion of the long dimension thereof defining a first plane, 42, and outer edges, 44a, and, 44b, opposite to inner edges 40a and 40b. Each member of a second pair of elongated flat stabilizer members (reference characters 80a, and, 80b in FIG. 1 B), not shown in FIG. 1A, having an inner edge radially attached to opposite sides of surface 36 of plunger 22 along at least a portion of the long dimension thereof defining a second plane (reference character, 46, in FIG. 1 B), not shown in FIG. 1A, perpendicular first plane 42, and outer edge (reference characters, 82a, and 82b, of FIG. 1 B) opposite to inner edge (reference characters, 84a, and 84b, of FIG. 1B, respectively), not shown in FIG. 1A, the outer edges of the first pair of stabilizer members and the second pair of stabilizer members being disposed within a circle having a diameter smaller than the minor axis of bore 14 of tube 12. The stabilizing members assist in reducing tilting of shaft 23 as plunger 22 is moved through bore 14 such that tilting motion of the shaft in the bore of the barrel does not affect the fluid seal between the flexible sealing member and the bore.

Flexible sealing member, stopper, or barrel stopper, 48, has an elliptical cross section adapted to slidably move within bore 14 of tube 12 from open end 16 thereof and provide a fluid seal therewith, first end, 50, and second end 52. Cylindrical-shaped interior portion, 54, is adapted to rotatably receive disk-shaped member 26 of plunger 22 introduced through opening, 56, in first end 50 of sealing member 48. Interior recess, 60, having an inner surface adapted to rotatably receive stub 28 is formed in stopper 48 between cylindrical-shaped interior portion 54 and second end 52, and form a fluid seal with the outer surface thereof. Bore, 58, passes between interior portion 54 of sealing member 48 through second end 52. As will be described in more detail hereinbelow, rotation of the disk-shaped fluid control member 26 is confined to about 90° in cylindrical-shaped interior portion 54 when plunger 22 is rotated about the long dimension thereof, such that bore 58 in sealing member 48 is in fluid contact with bore 30 in plunger 22 through slot 35 in the vicinity of one end of the about 90° rotation. Stopper 48 does not rotate as plunger 22 is rotated.

Second disk-shaped member 37 and lip 21 cooperate to form a barrier for preventing plunger 22 from accidentally being pulled from barrel 12. Further, disk-shaped member 37 is disposed sufficiently close to or in contact with (adjacent) first or top surface 50 of barrel stopper 48 such that barrel stopper 48 is stabilized during motion thereof through barrel 12.

Dispensing member, 62, has septum-piercing spike, 64, at one end thereof with first bore, 66, and second bore, 68, exiting spike 64 through holes, 69, and, 70, respectively. First bore 66 passes through dispensing member 62 and exits second end, 72, thereof. Dispensing member 62 is attached to or integrally formed with the first end 32 of plunger 22 such that first bore 66 is in fluid communication with bore 30 in plunger 22. Second bore 68 exits dispensing member 62 through exterior face, 74, thereof, forming thereby pressure relief port, 76. Pressure relief port 76 may be fitted with a venting cap containing a filter, as will be described hereinbelow. Clip, 78, holds a vial having a septum (not shown in FIG. 1A) in place for the transfer procedures described hereinbelow. Dispensing member 62, and infuser containers of various types are readily available components from medical and other component suppliers, and may be purchased with Luer-lock-compatible fittings in sterile packaging.

Figure 1B:
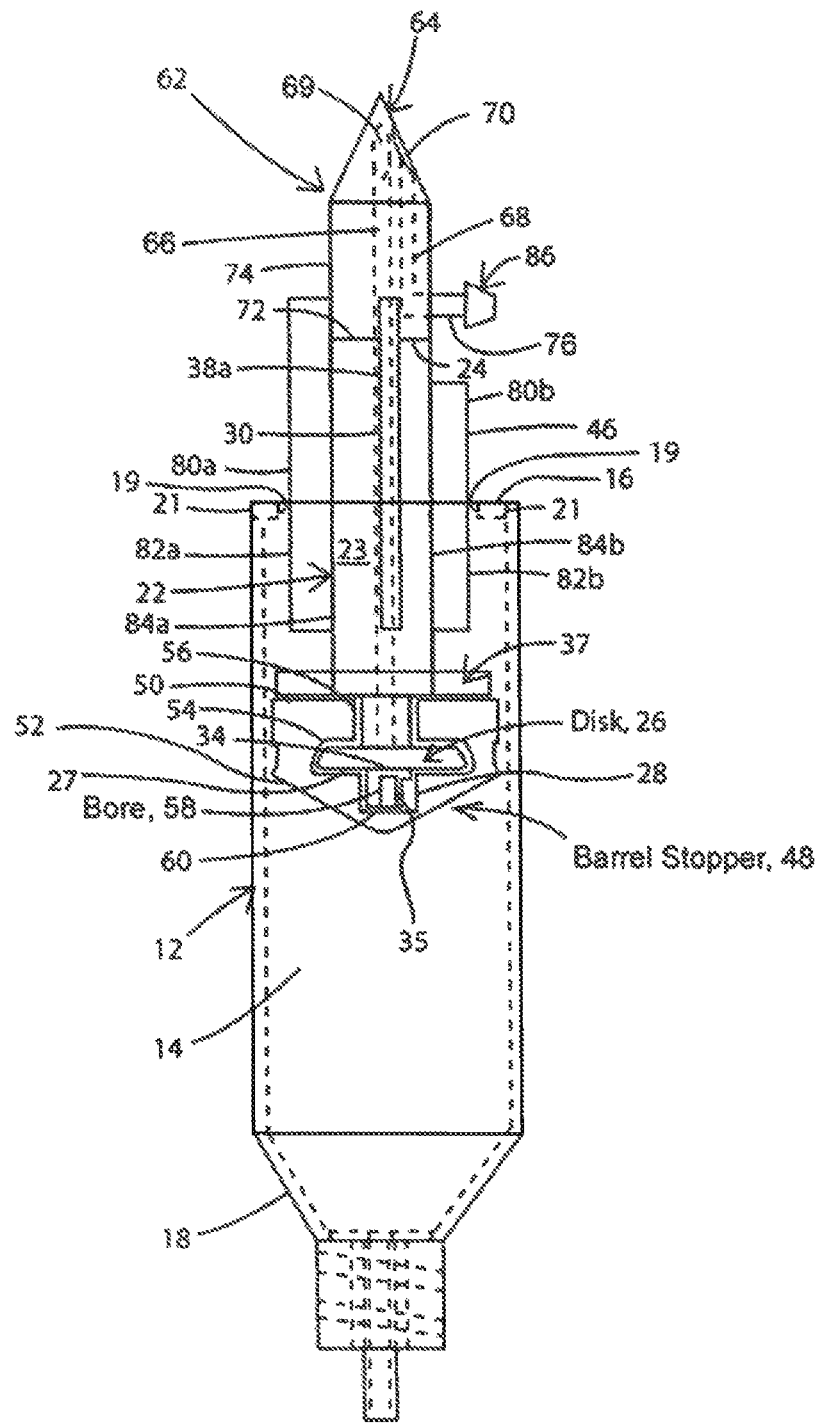
FIG. 1B is a schematic representation of a side view of the embodiment of the present invention shown in FIG. 1A hereof.

FIG. 1B is a schematic representation of the side view of the embodiment of the apparatus shown in FIG. 1A hereof, illustrating the second pair of elongated flat stabilizer members 80a and 80b, having inner edges 84a and 84b radially attached to opposite sides of surface 36 of plunger 22 along at least a portion of the long dimension thereof defining second plane 46, perpendicular first plane 42 (shown in FIG. 1A), and outer edges 82a and 82b opposite to inner edges 84a and 84b, respectively, the outer edges of the first pair of stabilizer members and the second pair of stabilizer members being disposed within a circle having a diameter smaller than the minor axis of bore 14 of tube 12, and smaller than the radius of the inner surface of lip 21 such that plunger 22 can be moved through bore 14. Shown also in FIG. 1B is venting orifice, 86, in fluid communication with the pressure relief port 76 for opening and closing pressure relief port 76. Orifice 86 may contain a filter element (not shown in FIG. 1 B) effective for filtering gaseous and other materials exiting from port 76.

Figure 1C:
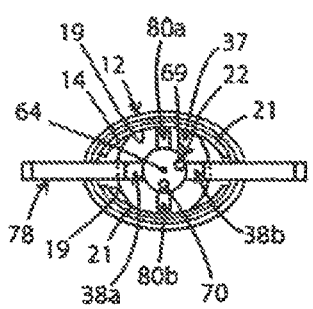
FIGS. 1C and 1D are schematic representations of the top view and bottom view of the embodiment of the apparatus shown in FIG. 1A hereof, respectively.
Figure 1D:
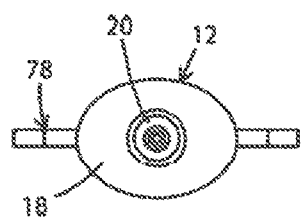

FIGS. 1C and 1D are schematic representations of the top view and bottom view of the embodiment of the apparatus shown in FIG. 1A hereof, respectively. As may be observed from FIG. 1C, stabilizer members 38a, 38b, 80a, and 80b have the same widths, or radial dimensions from the center of plunger 22, which permits outer edges, 44a, 44b, 82a, and 82b, respectively, to freely move inside of lip 21, as plunger 22 is moved through bore 14 of barrel 12, while the diameter of disk 37 is such that the disk can freely move in bore 14 of barrel 12 as plunger 22 is moved through bore 14 of barrel 12, under lip 21. As mentioned hereinabove, lip 21 is co-extensive with at least a portion of the opening of bore 14, and extends into the bore an amount effective for engaging disk 37 such that plunger 22 cannot be accidentally pulled from the bore, while enabling plunger 12 including oval-shaped stopper 48 and disk 37 to be inserted into the bore, albeit with some manipulation.

Opposing inward facing lips or protrusions 21 may occupy only a small portion opposing regions inside of bore 14 in the vicinity of the minor axis thereof such that one pair of opposing stabilizing members is blocked from rotating past opposing protrusions 21 in one direction, but free to rotate in the opposite direction until the second pair of opposing stabilizing members is blocked from further motion by protrusions 21. Stopper 48 does not rotate as plunger 22 is rotated.

The diameter of disk 37 is chosen such that the disk can move in bore 14 of barrel 12 under lip (protrusion) 21. As mentioned hereinabove, lip 21 is co-extensive with at least a portion of the opening of bore 14, and extends into the bore an amount effective for engaging disk 37 such that plunger 22 cannot be accidentally pulled from the bore, while enabling plunger 12 including oval-shaped stopper 48 and disk 37 to be inserted into the bore, again with some manipulation. Disk-shaped member 37 is disposed sufficiently close to or in contact with (adjacent) top surface 50 of barrel stopper 48 such that barrel stopper 48 is stabilized during motion thereof through barrel 12.

As may be observed from FIGS. 1C and 1 D, the rotation of plunger 22 is kept to approximately 90°, since two of the stabilizing members prevent further rotation of shaft 22 by contacting lip 21. Clearly, limitation of rotation of plunger 22 to larger or smaller angles is possible.

Figure 2:
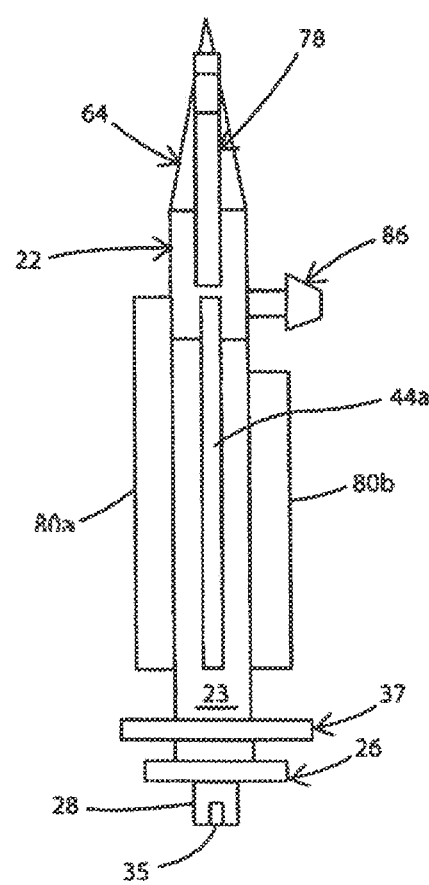
FIG. 2 is a schematic representation of the side view of plunger shown in FIG. 1B hereof.

FIG. 2 is a schematic representation of the side view of plunger 22 shown in FIG. 1B hereof. It is to be noted that disk 37 is shown as slightly smaller in diameter than stopper 48 in FIG. 1A since stopper 48 is elliptically shaped and the long dimensions of stopper 48 and barrel 12 are being viewed, while in FIG. 1B, disk 37 is shown as having the same diameter as stopper 48.

Figure 3A:
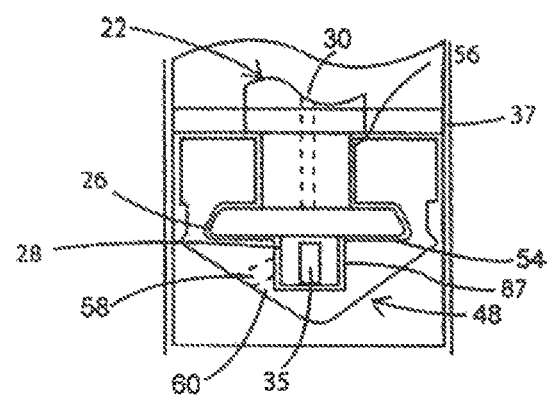
Figure 3B:
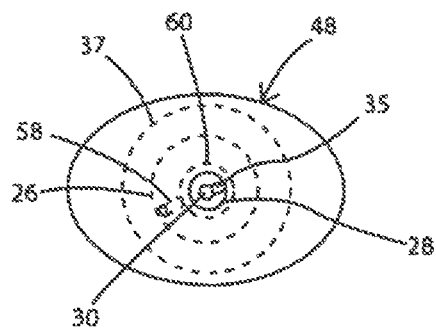
FIG. 3B is a schematic representation of the bottom view thereof.

FIG. 3A is schematic representation of the side view of stopper 48 shown in FIG. 1B hereof, while FIG. 3B is a schematic representation of the bottom view thereof. Cylindrical stub 28, is illustrated as being located in recess 60, whereby the rotation of stub 28 in recess 60 of stopper 48 is limited by the plunger stabilizing members such that bore 30 in plunger 22 may be aligned with outlet bore 58 through slot 35 in stub 28 for passing fluids in either direction through stopper 48, or occluded by inner wall, 87, of recess 60.

Figure 4A:
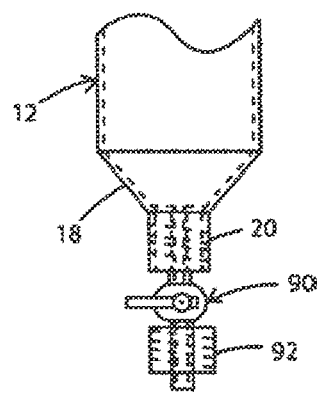
Figure 4B:
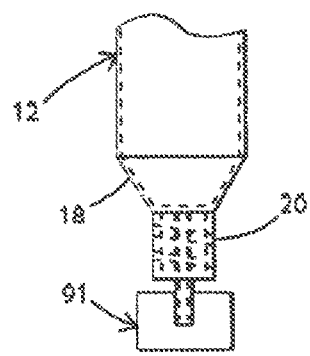
FIG. 4B is a schematic representation of a bottom view of a sided view of the barrel shown in FIG. 4A hereof, illustrating a cap attached to the exit port Luer connection for preventing flow of fluid therethrough.

FIG. 4A is a schematic representation of a side view of barrel 12 of the present invention illustrating valve, 90, attached to exit port Luer connection 20 of barrel 12, and having Luer connection, 91, for attachment of an infuser or other container, as an example, not shown in FIG. 4A, while FIG. 4B is a schematic representation of a side view of barrel 12 closed off by removable plug, 92.

Figure 5A:
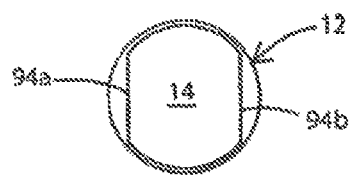
Figure 5B:
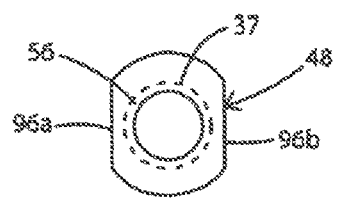
FIG. 5B is a schematic representation of a top view of the stopper for sealably moving within the bore of the barrel illustrated in FIG. 5A hereof.

FIG. 5A is a schematic representation of the top view of another embodiment of the barrel of the present invention. In this embodiment, bore 14 of barrel 12 has a circular cross section having at least one flat portion, 94a, 94b, effective for keeping barrel stopper 48, from turning when shaft 23, not shown in FIG. 5A, is rotated. FIG. 5B is a schematic representation of a top view of stopper 48 adapted for sealably moving within bore 14 of barrel 12 illustrated in FIG. 5A hereof. The remaining elements of embodiment of the mixing and dispensing apparatus hereof may be as described hereinabove. In particular, apparatus for the control of the rotation of shaft 23 to align shaft bore 30 with stopper bore 58 to permit flow of fluid into or out of apparatus 10, or for blocking fluid flow has been described hereinabove.

Embodiments of the present apparatus may be used as follows:

A. For vials of medications in powder form:
1. Barrel 12 of apparatus 10 is filled under sterile conditions with a chosen quantity of diluent into the lower chamber by drawing plunger 22 back. Valve 90 is then closed.
2. A medication vial is securely attached to dispensing member 62 using spike 64 to pierce the septum of the vial, and clip 78 to hold the vial.
3. To add the diluent into the vial, apparatus 10 is oriented such that the septum of the medication vial is facing upward. Plunger 22 is next rotated such that bore 30 in plunger 22 is aligned with outlet bore 58, through slot 35 in stub 28, and then depressed until stopper 48 reaches the closed end of bore 14 in barrel 12, thereby transferring the diluent from barrel 12 into the medication vial. The vial is then swirled to dissolve the powdered medication.
4. After an effective time for dissolution, apparatus 10 is next oriented such that the septum of the medication vial is facing downward. Plunger 22 is withdrawn to transfer the fluid from the vial into the barrel, and then rotated an amount effective for blocking bore 30 such that the fluid is prevented from re-entering the vial.
5. Apparatus 10 is then attached to a self-infusing elastomeric device, a conventional piggyback infuser, or other container, and valve 90 is opened and plunger 22 depressed to push the mixed contents into the elastomeric container.

B. For vials of medication in liquid form:
1. Valve 90 is first closed, after which plunger 22 is depressed such that stopper 48 is at the closed end of bore 14.
2. A medication vial is securely attached to the dispensing member 62, as described in Section A.
3. Apparatus 10 is oriented with the septum of the medication vial facing downward, and plunger 22 is first rotated such that bore 30 therein is aligned with outlet bore 58, in stopper 48 through slot 35 in stub 28, and then withdrawn such that liquid from the vial enters barrel 12.
4. Plunger 22 is rotated such that bore 30 is blocked such that the fluid cannot re-enter the vial.
5. Apparatus 10 is then attached to a self-infusing elastomeric device, a conventional piggyback, or other suitable container and valve 90 is opened. Plunger 22 is then depressed to push the mixed contents into the container.

C. Similar procedures may be followed in the situation where barrel 12 of apparatus 10 is purchased already filled with diluent, and Luer connection 20 is closed by removable plug 92, as illustrated in FIG. 4B.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for transferring liquids into and out of a vial having a septum, comprising:

a barrel having a bore with an elliptical cross section having a major axis and a minor axis, an open end, and a closed end, the closed end forming a port through which fluids flow;

a plunger comprising:

an elongated shaft having an axis; a first end, a first disk-shaped member forming a flat second end thereof, and an external surface between the first end and the first disk-shaped member; and having a first bore along the axis opening through both the first end and through the second end of said elongated shaft;

the flat second end having a cylindrical stub thereon having a second axis collinear with the axis of said elongated shaft, and a second bore along the second axis in fluid communication with the first bore, the cylindrical stub having an outer surface and a longitudinal channel therein between the second bore and the outer surface thereof;

a flexible stopper having an elliptical cross section adapted to slidably move within the bore of said barrel without rotating therein, and to provide a fluid seal therewith; a first end and a second end, a cylindrical-shaped interior portion opening to the first end and adapted to rotatably receive the first disk-shaped member; a recess adjacent to the cylindrical-shaped interior portion having an interior surface adapted to rotatably receive the cylindrical stub and to provide a fluid seal therewith; and a third bore passing between the interior surface of the recess through the second end of said stopper, such that when said elongated shaft is rotated to a chosen position, the third bore is in fluid contact with the longitudinal channel of the stub, and through the channel to the second bore; and a dispensing member having a septum-piercing spike at one end thereof with a fourth bore and a fifth bore exiting the spike, the fourth bore passing through said dispensing member and exiting a second end thereof, said dispensing member being attached to or integrally formed with the first end of said elongated shaft such that the fourth bore is in fluid communication with the first bore, the fifth bore entering said dispensing member and exiting through an exterior face thereof, forming thereby a pressure relief port.

2. The apparatus of claim 1, wherein the bore of said barrel has at least one inward facing lip having an inner surface having a radius in the vicinity of the open end thereof along at least a portion of the bore encompassing the minor axis.

3. The apparatus of claim 2, further comprising a second disk-shaped member disposed along said shaft adjacent to the first end of said stopper, said second disk-shaped member having a radius larger than the radius of the inner surface of the at least one lip.

4. The apparatus of claim 1, further comprising a first pair of elongated flat plunger stabilizing members each stabilizer member having an inner edge radially attached to opposite sides of the external surface of said shaft along at least a portion of the long dimension thereof defining a first plane, and an outer edge opposite to the inner edge; and a second pair of elongated flat stabilizer members each member having an inner edge radially attached to opposite sides of the external surface of said shaft along at least a portion of the long dimension thereof defining a second plane perpendicular to the first plane, and an outer edge opposite to the inner edge, the outer edges of the first pair of stabilizer members and the second pair of stabilizer members being disposed within a circle having a radius smaller than the radius of the inner surface of the lip of said barrel.

5. The apparatus of claim 1, further comprising a clip for securing said vial to said dispensing member.

6. The apparatus of claim 1, further comprising a filter element in fluid communication with the pressure relief port for filtering gaseous materials exiting therefrom.

7. The apparatus of claim 6, further comprising a venting cap containing said filter element for opening and closing the pressure relief port.

8. The apparatus of claim 1, wherein said barrel stopper comprises rubber.

9. The apparatus of claim 1, further comprising a valve for opening and closing the port in said barrel for passing fluids.

10. The apparatus of claim 1, further comprising a plug for closing the port in said barrel to passing fluids.

11. Apparatus for transferring liquids into and out of a vial having a septum, comprising:

a barrel having a circular bore with an axis, having a chosen circumference and at least one flat portion along the circumference of the bore extending over the length thereof, an open end, and a closed end, the closed end forming a port through which fluids flow;

a plunger comprising:

an elongated shaft having an axis; a first end, a first disk-shaped member forming a flat second end thereof, and an external surface between the first end and the first disk-shaped member; and having a first bore along the axis opening through both the first end and through the second end of said elongated shaft;

the flat second end having a cylindrical stub thereon having a second axis collinear with the axis of said elongated shaft, and a second bore along the second axis in fluid communication with the first bore, the cylindrical stub having an outer surface and a longitudinal channel therein between the second bore and the outer surface thereof;

a flexible stopper having at least one flat portion on the circumference thereof over a portion of the length of said stopper adapted to engage the at least one flat portion along the circumference of the bore such that said stopper slidably moves within the bore of said barrel without rotating therein, and to provide a fluid seal therewith; a first end and a second end, a cylindrical-shaped interior portion opening to the first end and adapted to rotatably receive the first disk-shaped member; a recess adjacent to the cylindrical-shaped interior portion having an interior surface adapted to rotatably receive the cylindrical stub and to provide a fluid seal therewith; and a third bore passing between the interior surface of the recess through the second end of said stopper, such that when said elongated shaft is rotated to a chosen position, the third bore is in fluid contact with the longitudinal channel of the stub, and through the channel to the second bore; and a dispensing member having a septum-piercing spike at one end thereof with a fourth bore and a fifth bore exiting the spike, the fourth bore passing through said dispensing member and exiting a second end thereof, said dispensing member being attached to or integrally formed with the first end of said elongated shaft such that the fourth bore is in fluid communication with the first bore, the fifth bore entering said dispensing member and exiting through an exterior face thereof, forming thereby a pressure relief port.

12. The apparatus of claim 11, wherein the bore of said barrel has at least one inward facing circumferential lip having an inner surface having a radius in the vicinity of the open end thereof along at least a portion of the circumference of the bore.

13. The apparatus of claim 12, further comprising a second disk-shaped member disposed along the shaft adjacent to the first end of said barrel stopper, said second disk-shaped member having a radius larger than the radius of the inner surface of the at least one lip.

14. The apparatus of claim 11, further comprising a first pair of elongated flat plunger stabilizing members each stabilizer member having an inner edge radially attached to opposite sides of the exterior surface of said shaft along at least a portion of the long dimension thereof defining a first plane, and an outer edge opposite to the inner edge; and a second pair of elongated flat stabilizer members each member having an inner edge radially attached to opposite sides of the exterior surface of said shaft along at least a portion of the long dimension thereof defining a second plane perpendicular to the first plane, and an outer edge opposite to the inner edge, the outer edges of the first pair of stabilizer members and the second pair of stabilizer members being disposed within a circle having a radius smaller than the radius of the inner surface of the lip of the bore of said barrel, and smaller than a distance from the axis to the at least one flat portion.

15. The apparatus of claim 11, further comprising a clip for securing said vial to said dispensing member.

16. The apparatus of claim 11, further comprising a filter element in fluid communication with the pressure relief port for filtering gaseous materials exiting therefrom.

17. The apparatus of claim 16, further comprising a venting cap containing said filter element for opening and closing the pressure relief port.

18. The apparatus of claim 11, wherein said barrel stopper comprises rubber.

19. The apparatus of claim 11, further comprising a valve for opening and closing the port in said barrel for passing fluids.

20. The apparatus of claim 11, further comprising a plug for closing the port in said barrel to passing fluids.

21. Apparatus for transferring liquids into and out of a vial having a septum, comprising:
- a barrel having a bore with an elliptical cross section having a major axis and a minor axis, an open end, and a closed end, the closed end forming a port through which fluids flow, the bore further having two opposing inward facing lips having an inner surface having a radius in the vicinity of the open end thereof along at least a portion of the bore in the vicinity of the minor axis;
- a plunger comprising:
- an elongated shaft having an axis; a first end, a first disk-shaped member forming a flat second end thereof, and an external surface between the first end and the first disk-shaped member; and having a first bore along the axis opening through both the first end and through the second end of said elongated shaft; the flat second end having a cylindrical stub thereon having a second axis collinear with the axis of said elongated shaft, and a second bore along the second axis in fluid communication with the first bore, the cylindrical stub having an outer surface and a longitudinal channel therein between the second bore and the outer surface thereof;
- a first pair of elongated flat plunger stabilizing members each stabilizer member having an inner edge radially attached to opposite sides of the surface of said elongated shaft along at least a portion of the long dimension thereof defining a first plane, and an outer edge opposite to the inner edge;
- a second pair of elongated flat stabilizer members each member having an inner edge radially attached to opposite sides of the surface of said elongated shaft along at least a portion of the long dimension thereof defining a second plane perpendicular to the first plane, and an outer edge opposite to the inner edge, wherein the outer edges of the first pair of stabilizer members and the second pair of stabilizer members are disposed within a circle having a radius smaller than the minor axis of the bore and larger than the radius of the inner surface of the lips of said barrel;
- a flexible stopper having an elliptical cross section adapted to slidably move within the bore of said barrel without rotating therein, and to provide a fluid seal therewith; a first end and a second end, a cylindrical-shaped interior portion opening to the first end and adapted to rotatably receive the first disk-shaped member; a recess adjacent to the cylindrical-shaped interior portion having an interior surface adapted to rotatably receive the cylindrical stub and to provide a fluid seal therewith; and a third bore passing between the interior surface of the recess through the second end of said stopper;
- wherein the rotation of the first disk-shaped member is confined to a chosen amount in the cylindrical-shaped interior portion when said elongated shaft is rotated about the long dimension thereof in one direction with one pair of stabilizer members contacting the lips, and in the opposite direction with the other pair of stabilizer members contacting the lips, such that the third bore is in fluid contact with the longitudinal channel of the stub, and through the channel to the second bore in a portion of the chosen amount of rotation; and
- a dispensing member having a septum-piercing spike at one end thereof with a fourth bore and a fifth bore exiting the spike, the fourth bore passing through said dispensing member and exiting a second end thereof, said dispensing member being attached to or integrally formed with the first end of said elongated shaft such that the fourth bore is in fluid communication with the first bore, the fifth bore entering said dispensing member and exiting through an exterior face thereof, forming thereby a pressure relief port.

22. The apparatus of claim 21, further comprising a second disk-shaped member disposed along the shaft adjacent to the first end of said barrel stopper, said second disk-shaped member having a radius larger than the radius of the inner surface of the lips.

23. The apparatus of claim 21, further comprising a clip for securing said vial to said dispensing member.

24. The apparatus of claim 21, further comprising a filter element in fluid communication with the pressure relief port for filtering gaseous materials exiting therefrom.

25. The apparatus of claim 24, further comprising a venting cap containing said filter element for opening and closing the pressure relief port.

26. The apparatus of claim 21, wherein said barrel stopper comprises rubber.

27. The apparatus of claim 21, further comprising a valve for opening and closing the port in said barrel for passing fluids.

28. The apparatus of claim 21, further comprising a plug for closing the port in said barrel to passing fluids.

* * * * *